United States Patent [19]

Aigner

[11] Patent Number: 4,666,426
[45] Date of Patent: May 19, 1987

[54] DOUBLE LUMEN CATHETER FOR A DEVICE FOR IN-VIVO PURIFICATION OF BLOOD

[76] Inventor: Karl Aigner, Uhlandstr. 5, 6301 Pohlheim 1, Fed. Rep. of Germany

[21] Appl. No.: 885,409

[22] Filed: Jul. 14, 1986

Related U.S. Application Data

[60] Division of Ser. No. 689,611, Jan. 11, 1985, which is a continuation-in-part of Ser. No. 518,449, Jul. 29, 1983, Pat. No. 4,563,170.

[30] Foreign Application Priority Data

Jan. 12, 1984 [DE] Fed. Rep. of Germany ....... 3400874

[51] Int. Cl.⁴ .............................................. A61M 5/00
[52] U.S. Cl. .......................................... 604/5; 604/43; 604/283
[58] Field of Search ...................... 604/4, 5, 27, 43, 45, 604/158, 280, 283

[56] References Cited

U.S. PATENT DOCUMENTS

| | | | |
|---|---|---|---|
| 4,014,333 | 3/1977 | McIntyre | 604/5 |
| 4,037,599 | 7/1977 | Raulerson | 604/44 |
| 4,098,275 | 7/1978 | Consalvo | 604/5 |
| 4,270,535 | 6/1981 | Bogue | 604/44 |
| 4,493,696 | 1/1985 | Uldall | 604/43 |

*Primary Examiner*—Stephen C. Pellegrino
*Attorney, Agent, or Firm*—Keil & Weinkauf

[57] ABSTRACT

An especially designed double lumen catheter (10) for use in a device for in-vivo purification of blood, by means of which blood pumped out of a vein is subjected to intensive ultrafiltration and the retentate, together with a quantity of a substitute fluid roughly corresponding, volumetrically, to the filtrate, is returned to the vein.

The double lumen catheter (10) with a coaxial arrangement of the two catheter tubes (13, 14) is so designed that the outer tube (14) is shorter than the inner tube (13) which latter forms the open catheter tip (12). The inner tube (13) is 4–6 cm longer than the outer tube (14) and, beginning from the tip (12), it has 4 pairs of lateral openings (11) at mutual spacings of between 8 and 12 mm. The outer tube (14) at its end has, over a length of 3.5–6 cm, 4 pairs of lateral openings (11) at a spacing of 8–12 mm each and at the smooth transition from the outer tube (14) to the inner tube (13) there is provided a contrast ring (15), of a material which under X-ray radiation is detectable through contrast formation. At the other end of the catheter (10) the inner tube (13) is made longer than the outer tube (14), for the connection of a two-way connecting member.

4 Claims, 4 Drawing Figures

DOUBLE LUMEN CATHETER FOR A DEVICE FOR IN-VIVO PURIFICATION OF BLOOD

This is a division of application Ser. No. 06/689,611, filed Jan. 11, 1985, which in turn is a continuation-in-part of application Ser. No. 06/518,449, filed July 29, 1983, U.S. Pat. No. 4,563,170.

Subject of the invention is an improved double lumen catheter for a device for the in-vivo purification of blood in which blood pumped out of a vein is subjected to intensive ultrafiltration and the retentate together with a quantity of substitute fluid roughly corresponding, volumetrically, to the filtrate is reintroduced to the vein. The device is particularly suited to filter out agents introduced in high concentration, in intra-arterial chemotherapy, before the venous blood reaches the heart and subsequently the circulatory system of the body.

Ultrafiltration of human blood in case of kidney failure to bring about a substitute function of the liver, is known. In this process blood is taken from an artery and, under its own pressure, passed through an ultrafilter or a so-called hemofilter, and the retentate is reintroduced, if desired together with a substitute fluid, into a vein. Pumps have also been interposed where the withdrawal and the reintroduction of blood are to be carried out from a single blood vessel.

In order to make this possible numerous double lumen catheters have been developed.

In German patent application DE-OS No. 3,010,841 a double cather has been described the catheter tubes of which are formed to be slidable with respect to each other and which can be used for the vein puncture for hemodialysis. Because of the slidability of the individual catheters the inlet openings or the outlet opening of the individual catheters can be placed at their tips, upon insertion into a blood vessel, in such a spacing with respect to each other that the blood reintroduced into the blood vessel does not reach the range of the withdrawal location.

From European application EP-OS No. 0 025 704 a double lumen catheter is known the lumens of which are formed to be coaxially slidable relative to each other so that only one portion needs to be introduced into the blood vessel. The inner lumen may be replaced without the necessity of withdrawing the outer lumen having the larger diameter from the blood vessel. The catheter tip is open and along the catheter there are provided, in addition, several lateral openings which with the two lumens, make simultaneous withdrawal and reintroduction of blood possible.

In French patent specification FR-PS No. 2 297 640 a double lumen catheter has been described in which one of the catheter tubes is enlarged to form a balloon. The balloon which consists of an elastic material is enlarged by the pressure of the reintroduced liquid to such an extent that it contacts the wall of the vessel and blocks the flow: The withdrawal location in front of the balloon is spatially separated in this fashion from the reintroduction location which lies behind the balloon. This design has the decided disadvantage that the blood vessel is completely blocked so that an undesired back pressure is produced and that also in the reintroduction of the blood from the second catheter tube into the vessel, an inhomogeneous flow profile is created.

In German patent application No. P 32 28 438 a double lumen catheter has been described.

In this catheter the first catheter part has a closed tip and a plurality of openings laterally provided in the vicinity of the tip. The second catheter lumen is located in the first and it terminates, with two or more openings, in the outer wall of the first catheter tube. The distance between the lateral opening of the first catheter tube farthest removed from the catheter tip and the nearest opening of the second catheter tube is 40-50 mm. The end openings of the second catheter tube in the wall of the first catheter tube are as large as the cross-section of the second tube.

A number of disadvantages have shown up in using this catheter in the in-vivo purification of blood. In this technique the catheter is used in combination with a hose from the first catheter part connected by way of an interposed first hose pump with the input side of an ultrafiltration filter; a second hose connecting the output side of the ultrafiltration filter with the second catheter lumen for the reintroduction of the retentate; a supply line, with an inserted second hose pump, for substitute fluid terminating in the hose line behind the filter; a supply line for anticoagulants terminating in the hose line before the filter; and an outlet line for the filtrate from the ultrafiltration filter terminating by way of a precisely adjustable valve in a measuring container.

These disadvantages, in particular, are in the nature of manufacturing difficulties relating to the coaxial arrangement of the catheter tubes and the reliable fitting of the ends of the inner lumen into openings of the outer wall of the second, outer lumen. It has also been found that the conditions applying to the inflow through the lateral openings in the vicinity of the catheter tip upon introduction of the catheter into the vena cava in immediate proximity to the heart, are still subject to improvement if, in intra-arterial chemotherapy, especially in tumor treatment the suitable chemotherapeutics are applied to the desired treatment location in as high a concentration as possible and, downstream of the treatment location, have to be filtered out again from the venous blood of the vena cava in order to avoid toxic effects and side reactions downstream of the treatment location.

OBJECT AND SUMMARY OF THE INVENTION

An object of the invention is the further improvement of the double lumen catheter in order to minimize flow disturbances within the blood vessel in the range of the blood withdrawal as well as blood reintroduction, as much as possible.

This object is attained by means of a double lumen catheter with a coaxial arrangement of the two catheter parts in which the outer tube is shorter than the inner tube forming the open catheter tip and which has lateral suction openings. The novel feature consists in that the inner tube is 4–6 cm longer than the outer tube and, beginning from the tip, 4 pairs of lateral apertures are provided at a mutual spacing of between 8 and 12 mm each; that the outer tube at its end has, over a length of 3.5–6 cm, 4 pairs of lateral apertures at a mutual spacing of 8–12 mm; and that at the smooth transition from the outer tube to the inner tube there is provided a ring of a material which is detectable, through contrast formation, under X-ray radiation.

Preferably the inner tube is 6 cm longer than the outer tube and the bores which are provided in pairs opposite each other are located on an end portion of the catheter inner tube, which is approximately 3 cm long. The outer lumen or the outer catheter tube surrounds the inner tube whereby a smooth outer sliding transition from the inner tube to the outer tube is formed. The openings which are provided in pairs in the outer tube preferably are located opposite each other over a length of 4 cm.

As a matter of principle both the suction openings and the reintroduction openings may be relatively offset in pairs in order to achieve an even more uniform flow profile in the range of the suction and reintroduction portions.

In order to be able to regulate the position of the catheter in the blood vessel a so-called contrast ring is provided at the transition between the outer tube and the inner tube, this ring being made of a material which, under X-ray radiation, provides a contrast with the environment so that the location of the catheter in its introduced state is detectable. Suitable X-ray contrast producing materials are precious metals, gold being particularly preferred.

The catheter is formed as a double hose, the outer catheter tube serving as the suction hose and the inner catheter tube as the reintroduction hose. The cross-section of the two catheter parts may be made equal or different. However, an equally large cross-section is preferred. If the catheter is pushed up in the main vein from the groin until the catheter tip comes to lie before or in the right atrium of the heart it has been found particularly advantageous, in order to avoid flow-conditioned difficulties which may lead to the disturbance of the heart rhythm, to design the catheter tip as an open tip and to proVide additionally 4 pairs of lateral openings at predetermined mutual spacings. A spacing of 8-12 mm has been found to be particularly suitable. Particularly preferred is a mutual spacing of the pairs of 10 mm each. A similar arrangement of paired openings has also proved advantageous for the suction openings in the outer tube. In order to insure a sufficient spacing between withdrawal and return location in the blood vessel, the inner catheter tube is formed 4-6 cm longer than the outer tube. The total length of the catheter amounts to 65-70 cm, preferably 68 cm, the outer tube having a length of 62 cm, that is, also at the rear end of the catheter is the inner tube longer than the outer tube. The cross-section of the catheter tubes and the openings for the discharge and the re-introduction are formed so that a feeding power of at least 600 ml per minute can be handled without a major pressure drop. The lateral openings, in combination with an opening at the tip of the cather, prevent the occurrence of an excessive pressure jet effect at such feeding powers.

In order to insure a safe connection at the rear end of the catheter, a two-way connecting member is provided there. The ends of the catheter tubes are fixedly clamped in relatively offset relationship, in a sleeve-shaped connecting member the inner wall of which is larger than the outer diameter of the catheter inner tube so that between the catheter inner tube as inserted into the sleeve and the bore wall an annular gap is formed. The annular gap communicates with the inner bore of a laterally extending connecting stud. The lateral connecting stud may extend at a right angle, but it can also extend at an acute angle so that a Y-shaped connecting member results.

In order to make the clamping of the catheter tubes possible, the front end of the connecting member is formed with a conical taper and the outer hose is clamped by means of a cap nut which is designed to be screwed-onto an outer thread on the sleeve. Instead of a thread it is also possible to use a cap cone for the clamping, with the fixed connection between the cone of the sleeve, the outer tube of the catheter and the cap cone being produced by adhesive bonding. The catheter inner tube is clamped by means of a cone which is designed to be screwed into an inner thread at the rear end of the sleeve, this cone having a bore passing all the way therethrough and also having an outer thread. In this case too it is possible to forego a screw connection and to mount the cone by means of an adhesive material. Screw connections are preferable if the connecting member is made of metal. However the two-way connecting member may also be made of plastic material. In this instance adhesive connections are better suited than threads. However even in the case of plastic parts corresponding inner and outer threads may be provided. In the case of plastic materials, thermoplastic materials deformable by injection molding or casting are employed which in addition meet the requirements of medical engineering and are inert to body fluid and also are sterilizable.

The catheter is used in particular in combination with additional parts for intra-arterial chemotherapy. In this technique the venous blood is aspirated by means of a hose pump or so-called roller pump and is pressed at an increased pump pressure through a conventional ultra-filtration filter and the retentate is re-introduced into the inner tube at a quanity of 400-700 ml per minute. Since in the filtration 100-200 ml per minute of filtrate fluid simultaneously leave the outer filtration filter, the supply of a corresponding quantity of substitute fluid is required for compensation. In order to make this possible, the hose connection between the ultrafiltration filter outlet for the retentate and the catheter has a connection for substitute fluid, a second hose pump being provided in the connecting line in order to facilitate the introduction of a requisite amount of substitute fluid into the system. The discharge of filtrate is regulated by means of a precisely adjustable valve and the discharge line ends in a collecting container with measuring provisions in order to make the volumetric determination of the fluid quantity withdrawn from circulation, possible.

Between the aspirating hose pump and the catheter a supply line for anticoagulants, for example hepatine, terminates in the hose line. This hose line which is approximately one meter long has an inner diameter of 1.5 mm and an outer diameter of 3 mm and at its other end is connected to a precisely adjustable automatic injection mechanism.

The ratio of the free cross-section of the two catheter tubes is 1:1 to 2:1, preferably however 1:1. The inner diameter of the inner catheter tube is not below 3 mm and preferably is 4 mm so that in the area of the tip an outer diameter of approximately 3.5-5 mm results. The outer tube is slightly larger in order to form an annular gap between inner tube and outer tube.

The connection of the catheter to the hose pump or the outer filtration filter is by way of hose connections which are connected to the two-way connecting member at the rear end of the catheter. Upstream and downstream of the first hose pump which aspirates the blood and presses it into the filter two lined rubber diaphragms are, respectively, inserted into the hose connection in order to facilitate injection or withdrawal of control samples by means of injection needles. Further diaphragms of this kind may be provided in the filtrate line downstream of the ultrafiltration filter before the valve and in the hose connection for the retentate for the re-introduction into the catheter. In order to be better able to regulate the pressure and the filling of the system there may be provided between the hose pump and the ultrafiltration filter a hose piece of elastic material in pillow form, which expands under the pressure generated by the hose pump and the increase or decrease of the volume of which is a measure for the pressure generated by the pump as well as for the filling of the system.

It is of particular advantage for the observation of the degree of filling if a further pillow-shaped hose piece of this kind is provided in the hose line for the retentate to the catheter. The pillows also act as air bubble traps. In order to be able to compensate for heat losses due to cooling in the overall apparatus for the in-vivo purification of blood, there is provided, in an embodiment, in the resupply hose line a hose coil, approximately 3–7 m, preferably 5 m, in length, which is placed in a water bath kept at 40° C. This makes it possible to warm the filtered blood and the supplied substitute fluid to the desired body temperature.

The catheter may be made of materials conventional and suitable in the manufacture of catheters. Such materials are neutral with regard to body fluid, they may be sterilized without problems and they are sufficiently elastic but on the other hand also sufficiently rigid to be introduced in blood vessels. Suitable materials are polyolefins, polyfluorated carbohydrate polymers, synthetic rubbers, polyvinyl fluorides and the like. Particularly preferred materials for catheters are silicon rubber and implantable polyvinyl chloride. For the hose connection basically comparable materials are suitable, especially however polyolefins, fluorated carbohydrate polymers or polyvinyl chloride for the hoses. The hose pumps are commercially available or are so-called roller pumps in which the pumping action is produced by compression of the hose.

For the ultrafiltration filters, conventional ultrafiltration filters with conventional diaphragms are suited provided that the filter area and the filter power are sufficient to safely remove the required quantity of low-molecular products from the blood. The required filter area has an order of magnitude of 1–2.5 m$^2$, preferably 1.4–2.0 m$^2$. Especially preferred is a filter area of 2 m$^2$. Suitable diaphragms are those which pass substances up to a molecular weight of approximately 40,000 to 60,000 but block higher molecular substances. In special cases other diaphragxs may be employed which only pass low-molecular products up to a molecule size of approximately 20,000.

A catheter according to the invention is particularly suited for a device for use in connection with cystostatic drug filtration in intra-arterial chemotherapy. The overall device makes a systemic treatment with locally high concentrations possible, the cystostatic and the other therapeutically active substances, upon treatment being filtered out of the blood by means of ultrafiltration and toxic side effects thus being avoided. Such toxic side effects can arise particularly if these substances, with the blood, reach the heart and thence the circulatory system of the body.

BRIEF DESCRIPTION OF THE DRAWINGS

The invention will now be described in greater detail with reference to the drawings.

DETAILED DESCRIPTION OF THE PREFERRED EMBODIMENT

Figure 1:
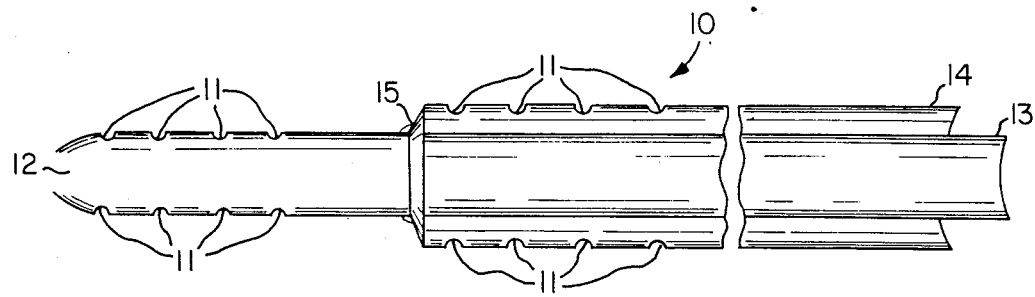
FIG. 1 shows a longitudinal section through the catheter according to the invention.

FIG. 1 shows the double lumen cather (10) in longitudinal section with the open end (12) of the inner tube (13) and the lateral openings (11) which are provided in pairs in the vicinity of the end. The outer catheter tube (14) surrounds the inner tube (13) over the main length of the catheter and it ends removed by approximately 6 cm from the tip of the inner tube (13). At the conical transition from the inner tube (13) to the outer tube (14) at the end of the outer tube a contrast ring (15) is provided. This ring makes it possible to detect the position of the catheter as inserted in the vein. The outer tube (14), too, has, in the vicinity of its end, 4 outlet openings (11) which are provided in pairs. At the rear end the inner tube (13) is formed longer than the outer tube (14) in order to make the connection to a two-way member possible.

Figure 2:
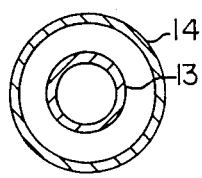
FIG. 2 shows a cross-section through the coaxially disposed catheter tubes.

FIG. 2 shows the coaxial arrangement of inner tube (13) and outer tube (14) along the main length of the catheter.

Figure 3:
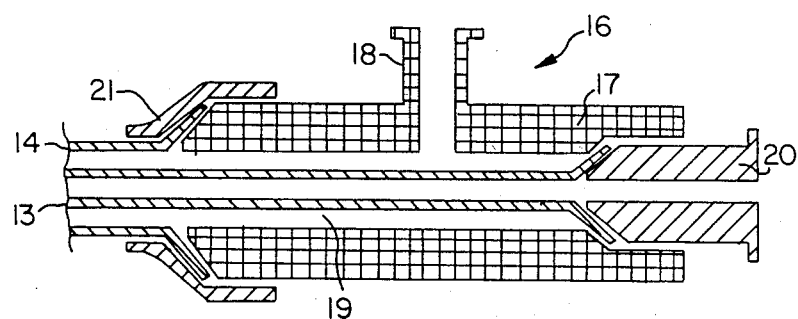
FIG. 3 shows the two-way connecting member in longitudinal section.

FIG. 3 shows, in schematic presentation, a longitudinal section through the two-way connecting member (16). The sleeve (17) has an inner bore (19) which is larger than the outer diameter of the catheter inner tube (13) and is approximately equal to the inner diameter of the catheter outer tube (14). At the rear end of the sleeve (17) the inner bore (19) is enlarged for the insertion of a conical stopper (20). The transition to the larger diameter is conical to enable the clamping, at this conical surface, of the inner tube (13) by means of the conical front face of the stopper (20). The stopper (20) has an inner bore extending therethrough and, at its other end, has a coupling for further hose connections, preferably a Luer coupling. A connecting stud (18) extends laterally from the inner bore (19) of the sleeve (17). In FIG. 3 this stud is shown extending at a right angle, however an acute angle is also possible. This stud, too, at its end preferably has a Luer coupling for the attachment of connecting hoses. The front end of the sleeve (17) is conically formed in order to enable the outer tube (14) of the catheter at this surface to be clamped by means of a cap cone (21). In order to make possible the connection of the cap cone (21) and the conical stopper (20) with the sleeve (17), correspondingly fitting threads, not shown in FIG. 3, are provided. Also an outer thread on the sleeve (17) in the vicinity of its front end, for enabling the cap nut (21) with an inner thread to be received, and at the end of the inner tube (19) on the portion with the larger diameter an inner thread, for enabling the conical stopper (20) with an outer thread to be screwed in. By means of a correspondingly conical design of the surfaces, clamping connections are possible which, if desired, may be improved, in their holding effect, by means of threads. In order to make the clamping connections permanent, the catheter tubes are additionally provided, on the inside as well as the outside, with suitable adhesive materials. However, the connection may also be effected by injection molding the connecting member to the hose ends.

Figure 4:
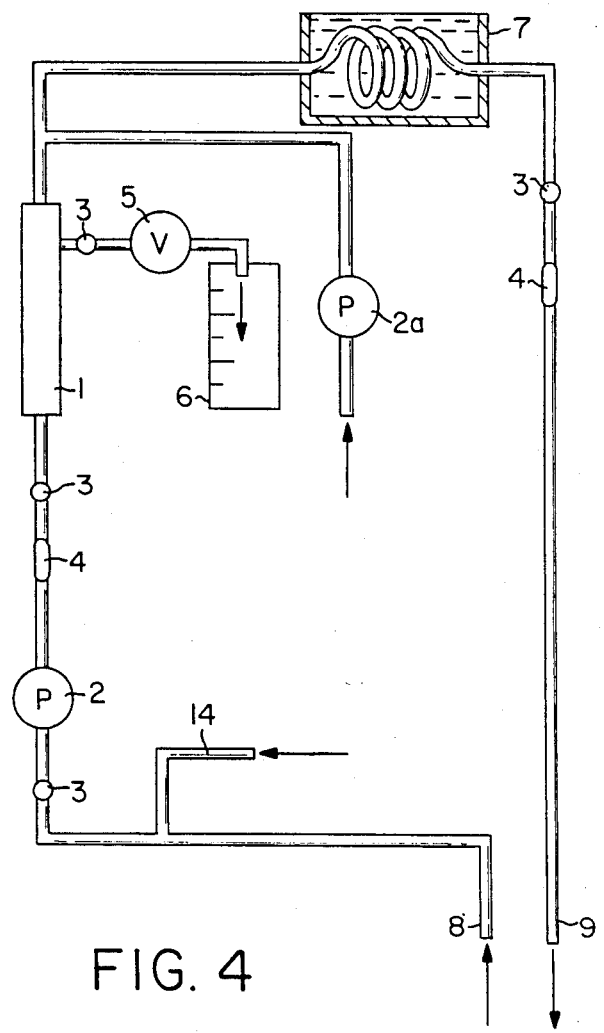
FIG. 4 shows a schematic overall view of the device which is employed in combination with the catheter.

FIG. 4 shows, in schematic presentation, the device which is employed in combination with the catheter. The double lumen catheter shown in FIG. 1 is connected to the hose connections (8,9) in such a fashion that the suction line is connected to hose (8) and the return line to hose (9). Venous blood is aspirated from the catheter outer tube by hose pump (2) by way of hose connection (8) and is pressed through the connecting hose into the ultrafiltration filter (1) and thence arrives at the catheter inner tube by way of hose connection (9). Supply line (14) for anticoagulant agents coming from an automatic injection apparatus terminates before the filter (1) in hose connection (8). Inserted in hose connection (8) before and after hose pump (2), respectively, are bordered rubber diaphragms (3), in order to make injectidns possible or to enable control samples to be drawn off by means of injection needles. Similar rubber diaphragms are provided in the filtrate line between the filter (1) and the valve (5) and in the hose connection (9) behind coil (7) which is placed in a water bath.

Numeral (4) denotes the elastic pillows for the control of the filling. From ultrafilter (1) there extends the filtrate line in which the precisely adjustable valve (5) is provided and which terminates in a collecting container (6) for the storage of the filtrate. The collecting container has an indicating scale and it has a capacity of 1–3 liters. Behind the ultrafiltration filter (1) there is provided in hose connection (9) the supply location for substitute fluid which is introduced by a second hose pump (2a). Hose pump (2a) aspirates the substitute fluid out of one or more storage vessels of sufficient capacity which are connected by means of hose connections. If desired, forks are provided by means of T-members, in order to enable a plurality of different substitute fluids to be used. The pumping in of the substitute fluid for which so-called Ringer solutions are preferably used is necessary because otherwise the large quantities of substitute fluid cannot be introduced into the system with the desired precision and speed. The power of the second hose pump (2a) is matched to the quantity of fluid leaving the system through the adjustable valve (5) in such a manner that volumetrically a loss of fluid is avoided as much as possible. As a matter of principle, however, it is also possible to introduce smaller or larger quantities of substitute fluids if this is required, in a special case, within the framework of the overall therapy.

In order to compensate for cooling losses there is preferably provided in hose line (9) a hose coil (7) which is disposed in a water bath the temperature of which is kept at approximately 40° C. In this fashion possible heat losses can be compensated in a simple manner so that the retentate, upon filtration, can be returned to the vein at the desired temperature. The hose connection between the catheter and the hose pump has a length of approximately 1.5 m, the hose distance between hose pump and filter is approximately 1 m, and approximately 2 m of hose connections without the hose coil are required for the connection of hose (9) to the catheter. The hose connections have an inner diameter of about 5 mm and an outer diameter of about 7 mm.

The connecting locations of the two-way connecting member have, the same as the hoses, color markings, for example red and blue, in order to avoid a transposition of connections.

The overall device is formed as a so-called filtration set together with the catheter. Preferably the set is marketed as a whole, sterile packaging being preferred in order to make instantaneous use of the entire combination possible. As a matter of principle, however, the set may also be separated into sterile and non-sterile packaged parts.

List of Reference Numerals

1—Ultrafilter, hemofilter
2,2a—Hose pumps
3—Inserted rubber diaphragm
4—Soft hose section for optical level monitoring, Hose pillow
5—Precisely adjustable valve
6—Collecting container for ultrafiltrate (measuring container)
7—Hose coil in water bath
8—Hose line from catheter
9—Hose line to catheter
10—Catheter
11—Paired openings
12—Front opening
13—Inner tube, catheter inner tube
14—Outer tube, catheter outer tube
15—Contrast ring
16—Two-way connecting member
17—Sleeve
18—Lateral connection
19—Inner bore
20—Conical stopper
21—Cap cone, Cap nut

I claim:

1. A double lumen catheter for the simultaneous withdrawal from and introduction into the vena cava, in the vicinity of the heart, of blood at a rate of at least 600 ml/min, while minimizing flow disturbances in the vein, in intra-arterial chemotherapy, with a coaxial arrangement of the two catheter tubes, in which the outer tube is shorter than the inner tube forming the open catheter tip, and has lateral suction openings,
   wherein the inner tube (13) is 4–6 cm longer than the outer tube (14),
   wherein, beginning from the tip (12) there are provided 4 pairs of lateral openings (11) at mutual spacings of between 8 and 12 mm each,
   wherein the outer tube (14) at its end has, over a length of 3.5–6 cm, 4 pairs of lateral openings (11) at a mutual spacing of 8–12 mm each, and
   wherein the transition from the outer tube (14) to the inner tube (13), which is smooth, includes a ring (15) of a material which is detectable, through contrast formation, under X-ray radiation.

2. A double lumen catheter as claimed in claim 1, with a branch connection at its rear end,
   wherein at the rear end of the catheter there is provided a connecting member (16) in the form of a sleeve (17) into which the end of the inner catheter tube (13) is inserted and to which the ends of the catheter tubes (13,14) are attached by clamping, the inner bore (19) of said sleeve being larger than the outer diameter of the catheter inner tube (13) so that between the catheter inner tube (13) as inserted into the sleeve (17) and the bore wall there is provided an annular gap,
   wherein said sleeve (17) has a lateral connecting stud (18) having a bore which is in communication with said annular gap.

3. A double lumen catheter insertable into the vena cava up to the vicinity of the heart, for use in a system for the in-vivo purification of blood in intra-arterial chemotherapy, in which large amounts of blood pumped out of the vena cava are subjected to ultrafiltration and, simultaneously with the withdrawal of blood from the vena cava, the filtrate is returned to the vena cava together with a requisite amount of substitute fluid;

wherein the double lumen catheter (10) is in the form of a coaxial arrangement of two substantially cylindrical catheter tubes (13,14) with the inner tube (13), which forms the open catheter tip (12), at its front end being 4–6 cm longer than the outer tube (14), wherein, beginning from the tip (12), there are provided in said inner tube (13) 4 pairs of lateral openings (11) at mutual spacings of between 8 and 12 mm each, wherein the outer tube (14) at its front end has, over a length of 3.5–6 cm, 4 pairs of lateral openings (11) at a mutual spacing of 8–12 mm each , and wherein the transition from the outer tube (14) to the inner tube (13), which is smooth, includes a ring (15) of a material which is detectable, through contrast formation, under X-ray radiation.

4. An in-vivo blood purification system for use in intra-arterial chemotherapy, said system comprising:

a double lumen catheter insertable into the vena cava up to the vicinity of the heart, the double lumen catheter (10) being in the form of a coaxial arrangement of two substantially cylindrical catheter tubes (13,14) forming an annular space therebetween, the inner tube (13), which forms the open catheter tip (12), at its front end being 4–6 cm longer than the outer tube (14), there being provided in said inner tube (13), beginning from the tip (12) 4 pairs of lateral openings (11) at mutual spacings of between 8 and 12 mm each, the outer tube (14) at its front end having, over a length of 3.5–6 cm, 4 pairs of lateral openings (11) at a mutual spacing of 8–12 mm each, and the transition from the outer tube (14) to the inner tube (13), which is smooth, including a ring (15) of a material which is detectable, through contrast formation, under X-ray radiation, and said system also comprising:

means (8, etc.) connectable to said annular space for pumping large amounts of blood out of the vena cava through said annular space, means (1, etc.) for subjecting said blood to ultrafiltration, and means (9, etc.) connectable to said inner tube (13) for returning, simultaneously with the withdrawal of blood from said annular space, the filtrate to the vena cava through said inner tube (13) together with a requisite amount of substitute fluid.

\* \* \* \* \*